(12) United States Patent
Jaffre et al.

(10) Patent No.: US 6,851,425 B2
(45) Date of Patent: Feb. 8, 2005

(54) EXHAUST PORT ASSEMBLY FOR A PRESSURE SUPPORT SYSTEM

(75) Inventors: Marcel D. Jaffre, Wendel, PA (US); Zachary D. Paul, Pittsburgh, PA (US); Winslow K. Duff, Export, PA (US); Michael Bobeck, Sarver, PA (US); Lance Busch, Trafford, PA (US)

(73) Assignee: Respironics, Inc., Murrysville, PA (US)

( * ) Notice: Subject to any disclaimer, the term of this patent is extended or adjusted under 35 U.S.C. 154(b) by 0 days.

(21) Appl. No.: 10/119,673

(22) Filed: Apr. 10, 2002

(65) Prior Publication Data

US 2003/0005931 A1 Jan. 9, 2003

Related U.S. Application Data

(60) Provisional application No. 60/293,735, filed on May 25, 2001.

(51) Int. Cl.$^7$ ............................................... A61M 16/00
(52) U.S. Cl. ........................ 128/204.18; 128/206.21; 128/207.12; 128/205.11
(58) Field of Search ..................... 128/204.18, 205.24, 128/204.26, 207.12, 206.12, 912, 206.21, 205.11

(56) References Cited

U.S. PATENT DOCUMENTS

| | | | |
|---|---|---|---|
| 1,632,449 A | 6/1927 | McKesson | |
| 2,254,854 A | 9/1941 | O'Connell | |
| 2,675,803 A | 4/1954 | Kaslow | |
| 2,928,388 A | 3/1960 | Jaroslaw | |
| 3,049,121 A | 8/1962 | Brumfield et al. | |
| 4,004,584 A | 1/1977 | Geaney | |
| 4,201,205 A | 5/1980 | Bartholomew | |
| 4,263,908 A | 4/1981 | Mizerak | |
| 4,266,540 A | 5/1981 | Panzik et al. | |
| 4,454,893 A | 6/1984 | Orchard | |
| D285,496 S | 9/1986 | Berman | |
| 4,655,213 A | 4/1987 | Rapoport et al. | |
| RE32,553 E | 12/1987 | Bennett et al. | |
| D293,613 S | 1/1988 | Wingler | |
| 4,850,346 A | 7/1989 | Michel et al. | |
| 4,944,310 A | 7/1990 | Sullivan | |
| 4,971,051 A | 11/1990 | Toffolon | |

(List continued on next page.)

FOREIGN PATENT DOCUMENTS

| | | |
|---|---|---|
| AU | A-48400/97 | 6/1998 |
| AU | A-59564/99 | 2/2000 |
| EP | 0 089 285 | 9/1983 |
| EP | 1 027 905 A2 | 8/2000 |
| GB | 880824 | 10/1961 |
| GB | 1395391 | 5/1975 |
| WO | WO 98/34665 | 8/1998 |
| WO | WO 00/38772 | 7/2000 |
| WO | WO 00/78381 A1 | 12/2000 |

OTHER PUBLICATIONS

Bird Products Corporation, Nightbird™ Nasal CPAP System Instruction Manual, California.

(List continued on next page.)

Primary Examiner—Glenn K. Dawson
Assistant Examiner—Darwin P Erezo
(74) Attorney, Agent, or Firm—Michael W. Haas (57) ABSTRACT

An exhaust port assembly comprising a conduit carries a flow of gas. A vent assembly having a fixed exhaust area is provided on the conduit for venting a flow of exhaust gas from within the conduit to ambient atmosphere. The vent assembly is configured so as to minimize noise associated with the flow of exhaust gas passing to atmosphere, diffuse the flow of exhaust gas passing to ambient atmosphere over a relatively large area, and minimize the area occupied by the venting assembly on the conduit.

11 Claims, 9 Drawing Sheets

U.S. PATENT DOCUMENTS

| | | | |
|---|---|---|---|
| 4,986,269 A | | 1/1991 | Hakkinen |
| 5,002,050 A | | 3/1991 | McGinnis |
| 5,020,532 A | | 6/1991 | Mahoney et al. |
| 5,438,981 A | | 8/1995 | Starr et al. |
| 5,546,933 A | | 8/1996 | Rapoport et al. |
| RE35,339 E | | 10/1996 | Rapoport et al. |
| 5,560,354 A | * | 10/1996 | Berthon-Jones et al. ............ 128/205.25 |
| 5,647,355 A | | 7/1997 | Starr et al. |
| 5,657,752 A | | 8/1997 | Landis et al. |
| 5,685,296 A | | 11/1997 | Zdrojkowski et al. |
| 5,878,743 A | | 3/1999 | Zdrojkowski et al. |
| 5,937,851 A | | 8/1999 | Serowski et al. |
| 5,937,855 A | | 8/1999 | Zdrojkowski et al. |
| 5,988,160 A | | 11/1999 | Foley et al. |
| 6,006,748 A | | 12/1999 | Hollis |
| 6,115,633 A | | 9/2000 | Lang |
| 6,412,488 B1 | * | 7/2002 | Barnett et al. ......... 128/207.13 |
| 6,460,539 B1 | * | 10/2002 | Japuntich et al. ...... 128/205.27 |
| 6,467,483 B1 | * | 10/2002 | Kopacko et al. ....... 128/207.12 |
| 6,691,707 B1 | * | 2/2004 | Gunaratnam et al. .. 128/206.21 |

OTHER PUBLICATIONS

Unknown, The Mapleson Breathing Systems.

Hillman, David R. et al., Continuous positive airway pressure: A breathing system to minimize respiratory work, 1985, USA.

Branthwaite et al., Continuous positive airway pressure: A new system, 1974.

Remmers et al., Nasal Airway Positive Pressure in Patients with Occlusive Sleep Apnea.

Map Medizintechnik fur Arzt und Patient, Aero–Click®, Germany.

Drager, E–Vent N, Aug. 1997, Germany.

* cited by examiner

EXHAUST PORT ASSEMBLY FOR A PRESSURE SUPPORT SYSTEM

CROSS-REFERENCE TO RELATED APPLICATIONS

This application claims priority under 35 U.S.C. §119(e) from provisional U.S. patent application Ser. No. 60/293,735 filed May 25, 2001.

BACKGROUND OF THE INVENTION

1. Field of the Invention

The present invention pertains to an exhaust port assembly for use in a single-limb pressure support system, and, in particular, to an exhaust port assembly with enhanced noise reduction and gas diffusion capabilities, while also minimizing size. The present invention also pertains to a pressure support system using such an exhaust port assembly.

2. Description of the Related Art

It is well known to treat a patient with a non-invasive positive pressure support therapy, in which a flow of breathing gas is delivered to the airway of a patient at a pressure greater than the ambient atmospheric pressure. For example, it is known to use a continuous positive airway pressure (CPAP) device to supply a constant positive pressure to the airway of a patient throughout the patient's respiratory cycle to treat obstructive sleep apnea (OSA), as well as other cardio-pulmonary disorders, such at congestive heart failure (CHF) and cheynes-stokes respiration (CSR). An example of such a CPAP device is the REMstar® and Solo®0 family of CPAP devices manufactured by Respironics, Inc. of Pittsburgh, Pa.

It is also known to provide a non-invasive positive pressure therapy, in which the pressure of gas delivered to the patient varies with the patient's breathing cycle. For example, a "bi-level" pressure support system provides an inspiratory positive airway pressure (IPAP) that is greater than an expiratory positive airway pressure (EPAP), which is the pressure is delivered during the patient's expiratory phase. Such a bi-level mode of pressure support is provided by the BiPAP® family of devices manufactured and distributed by Respironics, Inc. and is taught, for example, in U.S. Pat. No. 5,148,802 to Sanders et al., U.S. Pat. No. 5,313,937 to Zdrojkowski et al., U.S. Pat. No. 5,433,193 to Sanders et al., U.S. Pat. No. 5,632,269 to Zdrojkowski et al., U.S. Pat. No. 5,803,065 to Zdrojkowski et al., and U.S. Pat. No. 6,029,664 to Zdrojkowski et al., the contents of each of which are incorporated by reference into the present invention.

It is further known to provide an auto-titration positive pressure therapy, in which the pressure of the flow of breathing gas provided to the patient changes based on the detected conditions of the patient, such as whether the patient is snoring or experiencing an apnea, hypopnea or upper airway resistance. An example of a device that adjusts the pressure delivered to the patient based on whether or not the patient is snoring is the Virtuoso® CPAP family of devices manufactured and distributed by Respironics, Inc. This auto-titration pressure support mode is taught, for example, in U.S. Pat. Nos. 5,203,343; 5,458,137 and 6,087,747 all to Axe et al., the contents of which are incorporated herein by reference.

A further example of an auto-titration pressure support device that actively tests the patient's airway to determine whether obstruction, complete or partial, could occur and adjusts the pressure output to avoid this result is the Tranquility® Auto CPAP device, also manufactured by Respironics, Inc. This auto-titration pressure support mode is taught in U.S. Pat. No. 5,645,053 to Remmers et al., the content of which is also incorporated herein by reference.

Other modes of providing positive pressure support to a patient are known. For example, a proportional assist ventilation (PAV®) mode of pressure support provides a positive pressure therapy in which the pressure of gas delivered to the patient varies with the patient's breathing effort to increase the comfort to the patient. U.S. Pat. Nos. 5,044,362 and 5,107,830 both to Younes, the contents of which are incorporated herein by reference, teach a pressure support device capable of operating in a PAV mode. Proportional positive airway pressure (PPAP) devices deliver breathing gas to the patient based on the flow generated by the patient. U.S. Pat. Nos. 5,535,738; 5,794,615; and 6,105,573 all to Estes et al., the contents of which are incorporated herein by reference, teach a pressure support device capable of operating in a PPAP mode.

For purposes of the present invention, the phase "pressure support system", "pressure support device," or "positive pressure support" includes any medical device or method that delivers a flow of breathing gas to the airway of a patient, including a ventilator, CPAP, bi-level, PAV, PPAP, or bi-level pressure support system.

Figure 1:
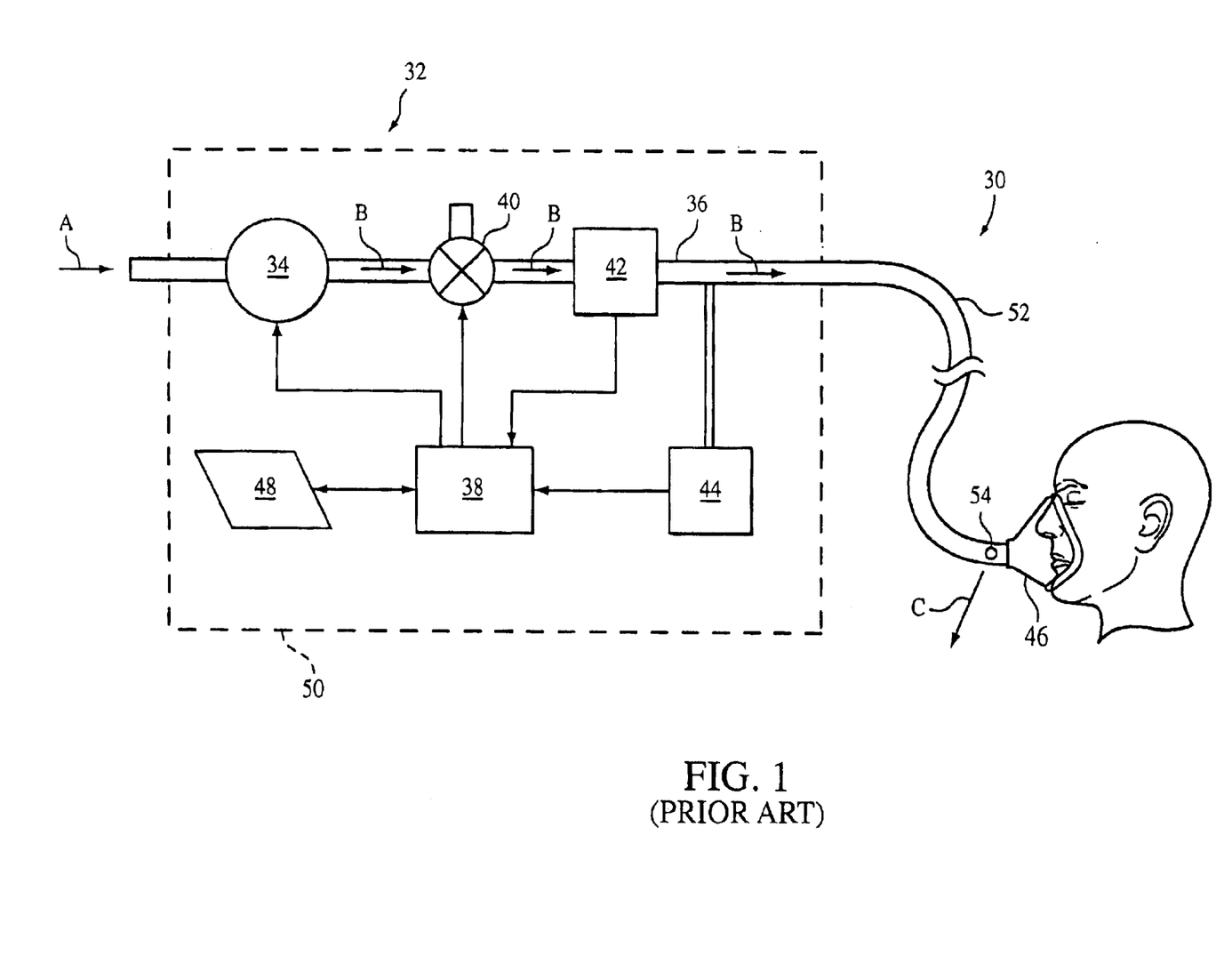
FIGS. 1 and 2 are schematic diagrams illustrating two embodiments of a conventional pressure support system.
Figure 2:
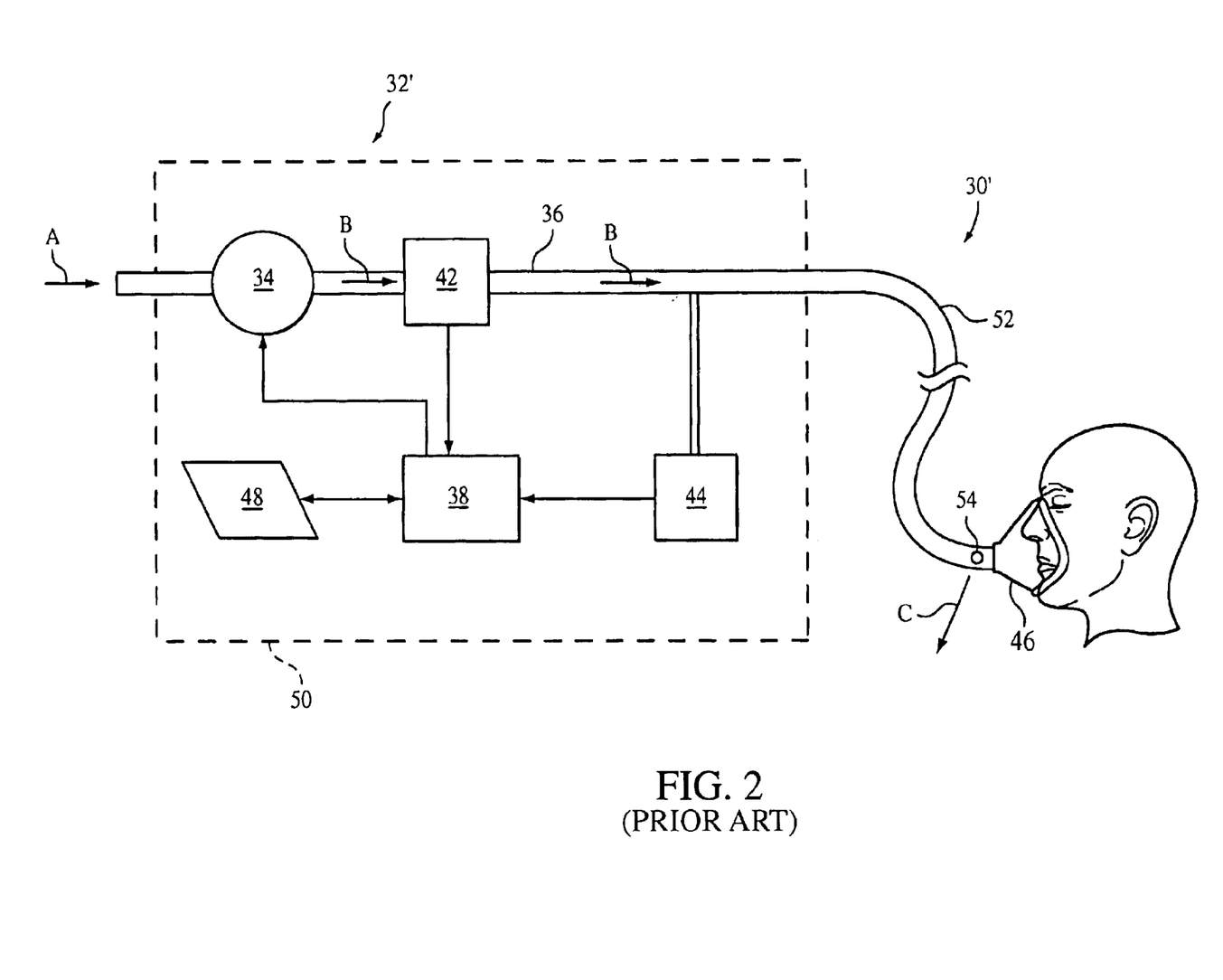

FIGS. 1 and 2 schematically illustrate two exemplary embodiments of conventional pressure support systems 30 and 30', respectively; either of is capable of providing any of the above positive pressure support therapies. The primary difference between these two embodiments is the technique used to control the pressure or flow of breathing gas provided to the patient.

Pressure support systems 30 and 30' include a pressure generating system, generally indicated at 32 and 32', that receives a supply of breathing gas from a breathing gas source, as indicated by arrow A, such as ambient atmosphere, and creates a flow of breathing gas at a pressure greater than ambient atmospheric pressure. The flow of breathing gas from pressure generator is indicated by arrow B. A pressure generator 34, such as a blower, impeller, drag compressor, fan, piston, or bellows, or other device that achieves this result, creates the flow of breathing gas at a pressure greater than the ambient atmospheric pressure. An exit conduit 36 communicates the flow of breathing gas from an outlet of pressure generator 34. Pressure generator 34 is a commonly a blower in which a fan or impeller is driven by a motor operating under the control of a controller 38, which is typically a microprocessor capable of executing stored algorithms.

In FIG. 1, the pressure or flow of breathing gas delivered to the patient is controlled, at least in part, by a pressure/flow controller 40 in conduit 36. Pressure/flow controller 40 is typically a valve that controls the pressure or flow of breathing gas by (1) exhausting a portion of the flow of breathing gas to atmosphere or to the inlet of pressure generator 34, (2) restricting the flow of breathing gas through conduit, or (3) a combination of these two functions. Controller 38 directs the operation of pressure/flow controller 40 to regulate the pressure or flow of breathing gas provided to the patient. Examples of suitable pressure controllers are taught in U.S. Pat. No. 5,694,923 to Hete et al. and U.S. Pat. No. 5,598,838 to Servidio et al.

In FIG. 2, the pressure or flow of breathing gas delivered to the patient is controlled, at least in part, by controlling the operating speed of pressure generator 34. This motor speed control technique can be used alone to control the flow or pressure of the breathing gas provided to the patient or it can be used in combination with a pressure controller 40, as discussed above. For present purposes, the combination of a pressure generator 34 and any of the above described techniques for controlling the flow or pressure of breathing gas provided to the patient, e.g., motor speed control, a pressure controller, or both, are referred to collectively as the "pressure generating system" or "pressure generating means," with the ultimate goal of the pressure generating system being to provide a flow of breathing gas to the airway of the patient at the desired pressure or flow rate.

A conventional pressure support system may also include at least one sensor capable of measuring a characteristic associated with the flow of breathing gas, the pressure of the breathing gas, a condition of a patient using the pressure support system, a condition of the pressure support system, or any combination thereof. For example, FIGS. 1 and 2 schematically illustrate a flow sensor 42 and a pressure sensor 44 associated with exit conduit 36. The output from such sensors are provided to controller 38 and used to control the rate of flow and/or pressure of the breathing gas delivered to the patient. For example, in a bi-level pressure support system, the transition from IPAP to EPAP and from EPAP to IPAP is triggered based on the changes in the patient's breathing cycle, which is detected by such sensors. For an auto-titration pressure support system, the output of one or more such sensors is used to determine when to raise and lower the pressure provided to the patient, and can be used to determine the magnitude of the change in pressure.

It is known that the location and number of such sensors can be other than that shown in FIGS. 1 and 2 while still providing feedback for the control of the pressure support system. For example, it is known to measure the pressure at or near a patient interface device 46, rather than near the pressure generating system 32, 32', as shown. In addition, it is known to monitor the operation of pressure generator 34 to determine the condition of the patient, such as whether the patient in breathing on the system. In which case, the functions of the pressure and/or flow sensors are effectively incorporated into the pressure generator monitoring function.

Although sensors 42 and 44 are described above as being a flow and pressure sensor, respectively, it is to be understood that other types of sensors can be used in pressure support systems 30 and 30'. For example, a microphone can be provided to detect sounds produced by the patient, which can be used, for example, in an auto-titration pressure support system to control the pressure of the breathing gas delivered to the patient. See, e.g., U.S. Pat. Nos. 5,203,343 and 5,458,137 both to Axe et al., the contents of which are again incorporated herein by reference.

Other sensors that can be used with the pressure support system include a temperature sensor that senses the temperature of gas anywhere in the breathing circuit, a current and/or voltage sensor for sensing the current/voltage of the signal provided to the motor in the pressure generator, and a tachometer that detects the rotational speed of the motor. These sensors are used, for example, to sense the condition of the patient, the flow or pressure of gas provided to the patient, or the operation of the pressure support system. Still other external sensors can include EMG electrodes provided on the patient, a respiratory belt or other motion sensor that measures movement of the chest and/or abdomen, and a motion sensor to detect patient movement, such as leg movement.

Conventional pressure support systems 30 or 30' also typically includes an input/output device 48 for communicating information to the user and for communicating information or commands to controller 38. An example of input/output device 46 is an LCD or LED display and manually actuated buttons provided on a housing, which is indicated by dashed line 50, of pressure support systems 30 and 30'. Of course, other types of input/output devices, such as a keypad, voice activated input device, audio outputs, lights, switches, and knobs are known for use in communicating information between the user and the pressure support device. In addition, a computer or printer terminal coupled to controller 38 can also constitute input/output device 48.

In a conventional pressure support system, a flexible conduit 52 is coupled to exit conduit 36. The flexible conduit forms part of what is typically referred to as a "patient circuit" that carries the flow of breathing gas from the pressure generating system to patient interface device 46. Patient interface 46 connects the patient circuit with the airway of the patient so that the elevated pressure gas flow is delivered to the patient's airway. Examples of patient interface devices include a nasal mask, nasal and oral mask, full face mask, nasal cannula, oral mouthpiece, tracheal tube, endotracheal tube, or hood.

In a non-invasive pressure support system, i.e., a system that remains outside the patient, a single-limb patient circuit, as shown in FIGS. 1 and 2, is typically used to communicate the flow of breathing (arrow B) with the airway of the patient. Because patient circuit 52 is a single-limb circuit, an exhalation port 54, also referred to as an exhalation vent, exhaust port, or exhaust vent, is provided in patient circuit 52 and/or patient interface 46 to allow exhaust gas, such as the exhaled gas from the patient, to exhaust to atmosphere, as indicated by arrow C.

A variety of exhalation ports are known for venting gas from a single-limb patient circuit. For example, U.S. Pat. No. Re. 35,339 to Rappoport discloses a CPAP pressure support system wherein a few exhaust ports are provided directly on the patient interface device, i.e., in the wall of the mask. However, these exhalation ports are relatively noisy due, for example, to the relatively turbulent passage of gas through the holes. In addition, this exhaust port configuration results in a relatively direct stream of exhaust gas being directed from the mask or patient circuit. Both noise and direct streaming of the flow of exhaust gas are undesirable, because a typical CPAP system is intended to be used while the patient is asleep. Sleep for the patient or the patient's bed partner is disturbed if there is excessive exhaust gas noise or if a stream of gas is directed at the patient or at the user's bed partner.

The exhaust port assembly described in published PCT application no. WO 98/34665 to Kwok attempts to minimize the noise associated with the leakage of exhaust gas. This is allegedly accomplished by providing an elastomeric ring around the perimeter of the exhaust vent. This exhaust port configuration, however, does not solve the problem of preventing a generally direct or concentrated stream of gas from being directed from the mask onto the user or the user's sleep partner.

U.S. Pat. No. 5,937,851 to Serowski et al., U.S. Pat. No. 6,112,745 to Lang, and published PCT application no. WO 00/78381 to Gunaratnam et al. all disclose exhalation ports for a positive pressure support system. Each of the exhalation ports taught by these references attempts to minimize noise by reducing the turbulence associated with the flow of exhaust gas through the exhalation vent. This is accomplished by providing a channel from the interior of the patient circuit to the ambient atmosphere that is specifically configured to baffle noise and/or reduce the turbulence in the exhaust flow. In addition, the exhalation ports taught by these references attempt to solve the problem of preventing a stream of gas from being directed onto the patient or onto the patient's bed partner by controlling the direction of the flow of exhaust gas. For example, each of these references teaches directing the flow of exhaust gas back along the patient circuit rather than directly outward away from the patient.

An exhaust vent entitled, "E-Vent N" and manufactured by Dräger Medizintechnik GmbH attempts to minimize noise by providing a large number of very small exhaust paths from the patient circuit to ambient atmosphere. More specifically, the E-Vent N exhaust port assembly includes several slits defined along the length of the patient circuit. Surrounding these slits are a number of rings that encircle the patient circuit and that are stacked one on top of the other. More specifically, each ring includes a series of grooves on its flat side, so that when the rings are stacked in this manner, the grooves in each ring form a very larger number of minutely sized exhaust paths to atmosphere, with the exhaust gas passing between adjacent rings. This configuration disperses the exhaust gas over a relatively large area due the large number of rings that are stacked on top of one another, so that the noise of the exhaust gas passing through the vent assembly is relatively low.

However, this exhaust port configuration is very complicated in that the stacked ring configuration is difficult to manufacture and maintain. Also, the minute exhaust paths defined between each ring are prone to clogging and cleaning is difficult. Finally, this design requires that the exhaust paths formed by the grooved rings occupy a relatively large area of the patient circuit to provide a sufficient flow of exhaust gas therefrom. This makes the exhaust port assembly bulky and heavy, and it does not minimize the amount of deadspace in the patient circuit.

SUMMARY OF THE INVENTION

Accordingly, it is an object of the present invention to provide an exhaust port assembly that overcomes the shortcomings of conventional exhaust vent devices. This object is achieved according to one embodiment of the present invention by providing an exhaust port assembly that includes a conduit having a first end and a second end for carrying a flow of gas and a venting means disposed between the first end and the second end of the conduit. The venting means has a fixed exhaust area for venting a flow of exhaust gas from within the conduit to ambient atmosphere. In addition, the venting means simultaneously minimizes noise associated with the flow of exhaust gas passing to atmosphere, diffuses the flow of exhaust gas passing to ambient atmosphere over a relatively large area, and minimizes the area occupied by the venting means on the conduit.

In one embodiment of the present invention, the venting means comprises a plurality of holes defined in the conduit. Each hole defines a direct path from the interior of the conduit to ambient atmosphere through the conduit. Preferably, the holes have a diameter in a range of 0.040 in. to 0.010 in. Within this range of diameters, the number of holes can vary depending on the specific exhaust rate to be achieved. For example, if the effective exhaust flow from the conduit is to be no greater than 67 liters per minute (lpm) when the pressure within the conduit is at 40 cmH$_2$O and at least 7.5 lpm when the pressure within the conduit is at 1.5 cmH$_2$O, there will be needed between 20 and 150 holes through the conduit over this range of sizes.

In another embodiment of the present invention, the venting means comprises an opening or slot defined in the conduit with a cap covering the slot, but spaced apart from the conduit, so that the cap and the conduit do not lie in the same plane. The cap and slot are sized and located relative to one another such that a gap is defined between the edge of the cap and the edge of the slot. This gap is defined on one or both sides of the cap and is preferably sized such that the distance from the edge of the cap and the edge of the slot is not greater than 0.020 in.

It is yet another object of the present invention to provide a pressure support system that does not suffer from the disadvantages associated with conventional systems using conventional exhaust port techniques. This object is achieved by providing a pressure support system that includes a pressure generator, a patient circuit, and an exhaust port assembly as described in the immediately preceding two paragraphs.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 3:
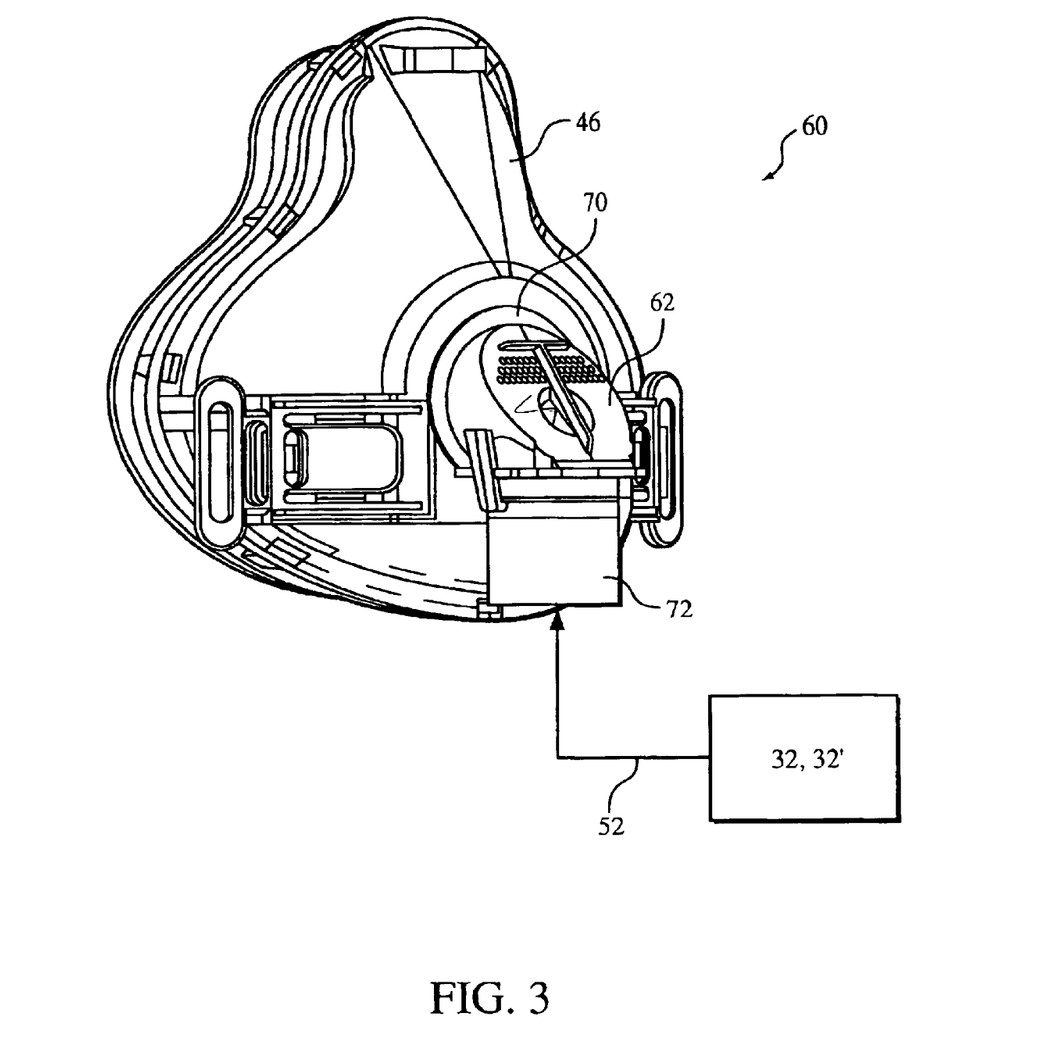
FIG. 3 is a perspective view of a mask and exhaust port assembly according to a first embodiment of the present invention.
Figure 4:
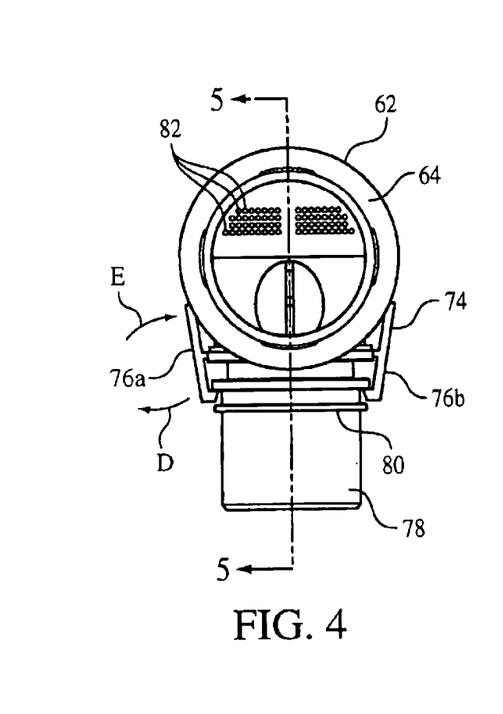
FIG. 4 is a front view of the exhaust port assembly of FIG. 3.
Figure 5:
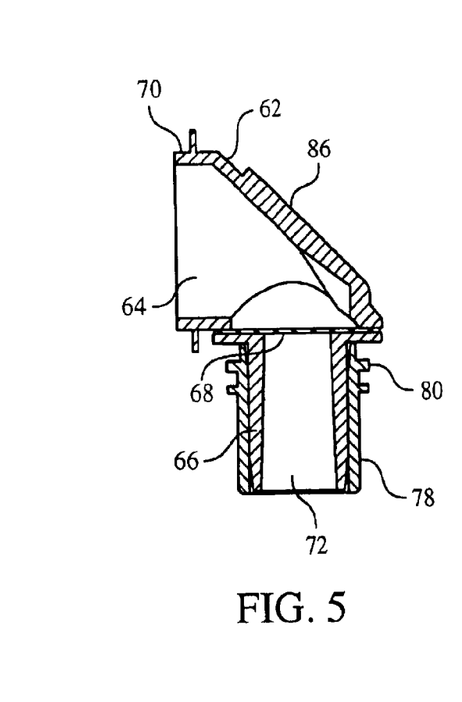
FIG. 5 is a cross-sectional view of the exhaust port assembly taken along line 5—5 of FIG. 4.
Figure 6:
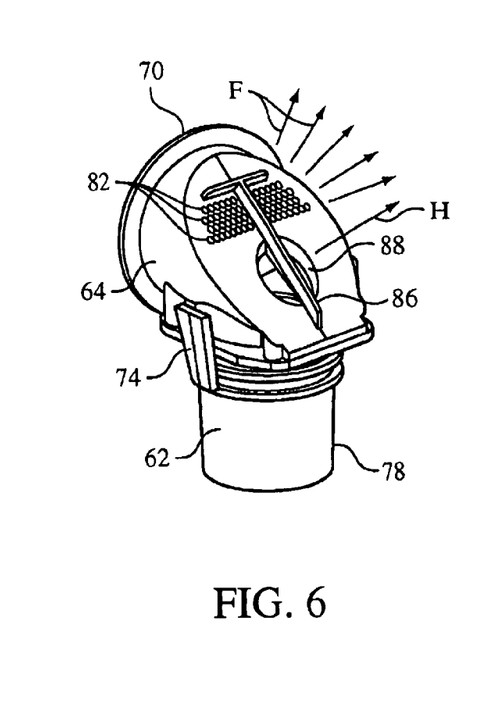
FIG. 6 is a perspective view of the exhaust port assembly of FIG. 3.
Figure 7:
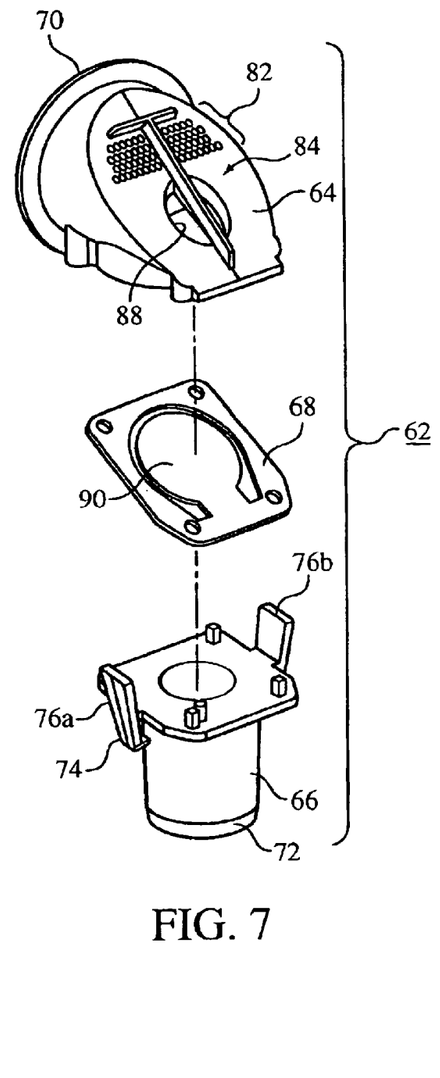
FIG. 7 is an exploded view of the exhaust port assembly of FIG. 3.
Figure 8:
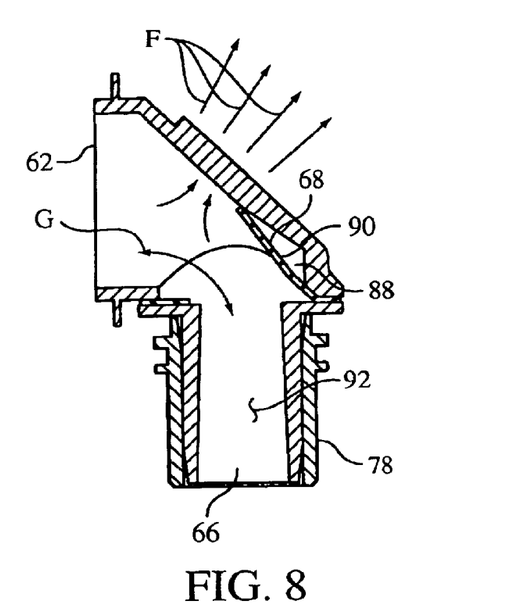
FIG. 8 is a cross-sectional view of the exhaust port assembly showing a first position of the valve member.

FIG. 3 schematically illustrates a first embodiment of a pressure support system 60 according to the principles of the present invention. Pressure support system 60 includes a pressure generating system 32, 32', a patient interface device 46, a patient circuit 52, and an exhaust port assembly 62. Pressure generating system 32, 32' corresponds to any conventional pressure generating system, such as those discussed above with respect to FIGS. 1 and 2. Similarly, the present invention contemplates that patient interface device 46 corresponds to any conventional patient interface device. For illustration purposes the patient interface device shown in FIG. 3 is a full face mask that covers the user's nose and mouth.

Exhaust port assembly 62, as shown in greater detail in FIGS. 4–9, includes a vent member 64, a conduit coupling member 66, and a valve member 68. Vent member 64 and conduit coupling member 66 are preferably joined to one another during the manufacturing process using any conventional technique so that valve member 68 is sandwiched therebetween. It is to be understood, however, that vent member 64 and coupling member 66 can be fixed to one another or formed from a single piece of material so that they are essentially one component. Furthermore, valve member 68 can be omitted if the functions provided by that valve, which are discussed in greater detail below, are not required.

The combination of vent member 64 and conduit coupling member 66 define a conduit having a first end 70 that is coupled to patient interface device 46 and a second end 72 that is coupled to patient circuit 52. In a preferred embodiment of the present invention, first end 70 is rotateably and permanently attached to patient interface device 46 using any conventional technique. Second end 72 is preferably selectively attachable to patient circuit 52. However, the present invention alternatively contemplates permanently attaching second end 72 to patient circuit 52 so that the conduit formed by exhaust port assembly 62 essentially becomes part of the patient circuit.

In the illustrated exemplary embodiment, exhaust port assembly 62 includes a quick release assembly 74 provided on conduit coupling member 66, so that the conduit coupling member can be readily attached and detached from an end of patient circuit 52, thereby allowing the wearer to uncouple himself or herself from the pressure support system without having to remove the mask and mask headgear from his or her head. In the illustrated exemplary embodiment, quick release assembly 74 includes a pair of flexible prongs 76a and 76b attached on opposite sides of conduit coupling member 66 and an adapter member 78 that attaches to the patient circuit. An end of each prong that engages the assembly to the patient circuit flexes outward, as indicated by arrow D, when a force is applied to the other end or the prong, as indicated by arrow E.

The end of patient circuit 52 is frictionally secured to adapter member 78, which is coupled to conduit coupling member 66 due to the engagement between the end of prongs 76a, 76b with an engagement member 80 provided on adapter member 78. In the illustrated embodiment, engagement member 80 is a ring. It is to be understood, however, that other configurations for engagement member 80, as well as prongs 76a, 76b, are contemplated by the present invention, including providing the prongs on adapter member 78 and providing the engagement member on coupling member 66.

In addition, the present invention contemplates eliminating adapter member 78 in favor of providing the components of the quick release assembly directly on the end of the patient circuit. Furthermore, the present invention contemplates other techniques for providing a quick connect/release function for attaching second end 72 of exhaust port assembly 62 to patient circuit 52, including, but not limited to, a purely frictional attachment, a slot and key interconnection, or any other conventional technique for releaseably coupling two conduits to one another.

Exhaust port assembly 62 includes a venting structure, also referred to as a venting means, disposed between first end 70 and second end 72 of the conduit for venting a flow of exhaust gas from within the conduit to ambient atmosphere. According to the embodiment illustrated in FIGS. 3–9, the venting structure includes a plurality of fixed diameter holes 82 defined directly through venting member 64 so that a continuous flow of exhaust gas can escape from within the exhaust port assembly to ambient atmosphere, as indicated by arrows F.

By providing a relatively large number of holes 82 as the exhaust ports, this embodiment of the present invention minimizes the noise associated with the flow of exhaust gas passing to atmosphere. More specifically, the relatively large number of holes allows the flow through any single hole to be relatively low, and the lower the flow through any one exhaust path, the less noise will be created by the gas passing through that exhaust path. In addition, this configuration for the exhaust port diffuses the flow F of exhaust gas passing to ambient atmosphere over a relatively large area, thereby avoiding the undesirable consequences associated with a relatively direct or concentrated flow of exhaust gas note above. Furthermore, by providing the plurality of holes in a relative compact area, namely on a planar surface 84 of vent member 64, the area occupied by the venting structure on the conduit is minimized. This is advantageous, as noted above, in it keeps the patient circuit relatively simple, light weight, and minimize deadspace, which is the space from the airway of the patient to the exhaust port where gas is not exhausted from the patient circuit or patient interface.

The present invention contemplates that the total exhaust area, i.e., the area of all of the exhaust paths defined by the holes combined, corresponds to that of conventional exhaust port assemblies. Of course, as with a conventional exhaust port, the total exhaust area can vary depending on the desired rate of exhaust flow. However, in normal operation as a pressure support device, such as a CPAP device, the maximum exhaust flow from the exhaust port assembly is preferably no more than 67 liters per minute (lpm) when the pressure within the patient circuit, i.e., conduit defined by the components of the exhaust port assembly, is 40 cmH$_2$O, which is a maximum pressure likely to be experienced during normal operation of a pressure support system. Similarly, the minimum exhaust flow should be at least 7.5 lpm when the pressure within the assembly is at 1.5 cmH$_2$O. Therefore, the number of holes and the size of the holes should be selected to achieve these flow rates.

In an exemplary embodiment of the present invention, each hole has a fixed diameter in a range of 0.040 in. to 0.010 in. Within this range of sizes, the number of holes can be selected so achieve a desired exhaust flow for a certain pressure within the conduit. For example, in one conventional pressure support system, the effective exhaust flow is selected to be between 67 lpm and 7.5 lpm, when the pressure within the conduit is 40 and 1.5 cmH$_2$O, respectively. Over the above-identified hole dimensions, the number of holes needed to provided this exhaust flow will be between 20 and 150. In a preferred embodiment of the present invention, the holes are 0.025 in. in diameter and are no closer together than 0.025 in. It can be appreciated, however, that if higher exhaust flow rates are desired, this can be accomplished by increasing the number of holes, while keeping the diameter of the holes is in a range of 0.040 in. to 0.010 in.

As noted above, the number of holes can be increased or decreased. However, if the rate of exhaust, i.e., the flow, is to remain unchanged, the diameter of each hole should also be decreased or increased, respectively, to provide substantially the same exhaust path area depending on the number of holes. Because holes 82 are defined directly through the conduit, manufacturing and machining tolerances would limit how small the diameter of each hole can be made. In addition, the number of holes should not be made too great, otherwise the size of the holes must be made so small that the holes become susceptible to occlusion, for example, due to water or fluid bridges spanning the holes. Furthermore, the number of holes should not be made too small, otherwise the size of the holes becomes too large and the gas diffusion properties are lost.

The present invention contemplates that each hole 82 is a generally straight path from the interior of the conduit to ambient atmosphere. The present invention further contemplates that each hole 82 has a relatively constant diameter over the length of the path. However, other configurations for holes 82 are contemplated, such as having a diameter that decreases from the interior of the conduit toward an exterior thereof. While holes 82 are shown as being generally circular in shape, the present invention contemplates that the holes can have other shapes, such as square, oval, triangular, etc. Moreover, holes 82 need not all have the same shape, size or diameter.

As noted above, holes 82 are provided on planar surface 84 so that the exhaust gas flow F is dispersed in a direction generally away from the patient wearing patient interface device 46. Also, planar surface 84 provides a surface in which it is relatively easy to form holes 82. Preferably, a protrusion 86 is provided near holes 82 to prevent them from becoming blocked. It should be noted that the spacing between the hole and the pattern by which the holes are defined in the conduit can also be different than that shown in the figures. However, it is preferably that the spacing between the holes is not less than the diameter of the holes to ensure that the gas diffusion characteristics, and, hence, noise reduction, are maximized.

It is to be understood that the present invention contemplates other techniques for providing a plurality exhaust paths from the interior of the patient circuit to ambient atmosphere for maximizing the dispersion of the exhaust flow, while ensuring that each path has a relatively of relative small area and that the plurality of exhaust paths are located on a relatively small area of the patient circuit. For example, the present invention contemplates providing a relatively large opening in the conduit, with a screen disposed over this opening. The screen consists of a mesh having a plurality of holes defined therein. The number of holes defined by in the screen mesh and the size of these holes is chosen, as discussed above with respect to the holes 82, to achieve the desired exhaust flow at the operating pressures of the pressure support system.

As noted above, the exhaust port assembly of the present invention is intended for use with a variety of different types of mask, including a full face mask, which is a patient interface device that covers the patient's nose and mouth. It is common when using a full face mask, to provide a valve in the patient circuit that automatically allows the patient access to the ambient atmosphere in the event of a failure of the pressure support system. See, e.g., U.S. Pat. No. 5,438,981, which teaches the function of such a valve and describes several embodiments of such a valve.

To provide automatic access to the ambient atmosphere, exhaust port assembly 62 includes an auxiliary opening 88 defined in the conduit and having a relatively large diameter and valve member 68. During normal use, where the pressure support system is functioning properly, a cantilever member 90 of valve member 68 flexes, as shown to FIG. 8, to block auxiliary opening 88. If the gas pressure in an interior 92 of the conduit is greater than the ambient atmosphere, cantilever member 90 moves to the position shown in FIG. 8 to block opening 88, so that gas is able to flow between the patient and the pressure generating system, as indicated by arrow G.

Figure 9:
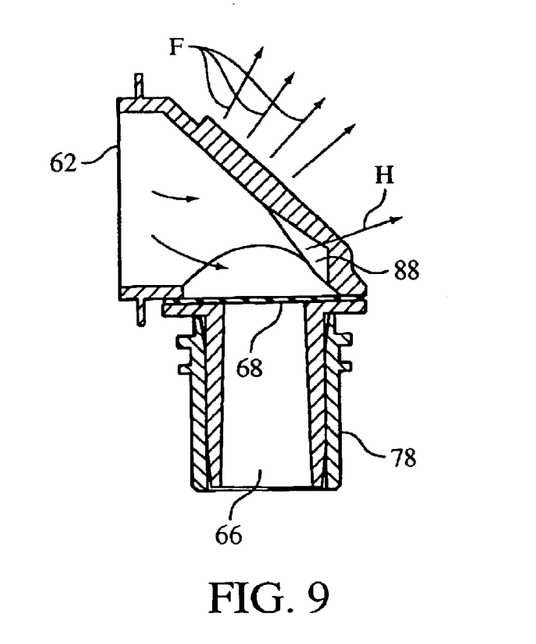
FIG. 9 is a cross-sectional view of the exhaust port assembly showing a second position of the valve member.

If, however, the pressure of the gas in interior 92 is not greater than ambient atmosphere, cantilever member 90 returns to its normal, undeflected position shown in FIG. 9 and unblocks auxiliary opening 88 so that the patient has access to the ambient atmosphere as indicated by arrow H. In this position, cantilever member 90 also blocks gas from flowing through the conduit toward the pressure support system. The spring force of cantilever member 90 tends to urge it toward the unflexed position shown in FIG. 9 to ensure that auxiliary opening 88 becomes unblocked if the pressure support system fails to provide an adequate supply of breathing gas.

It should be noted that the operation of valve member 68 to block and unblock auxiliary opening 88 and the patient circuit does not affect the operation of holes 82 in venting a continuous flow F of gas from the patient circuit. It is to be further understood, that a variety of configurations for auxiliary opening 88 and valve member 68 are contemplated by the present invention, so long as they function as discussed above. Furthermore, auxiliary opening 88 and valve member 68 can be eliminated if their function of providing automatic access to ambient atmosphere is not required; for example, if the patient interface device is a nasal mask only.

Figure 10:
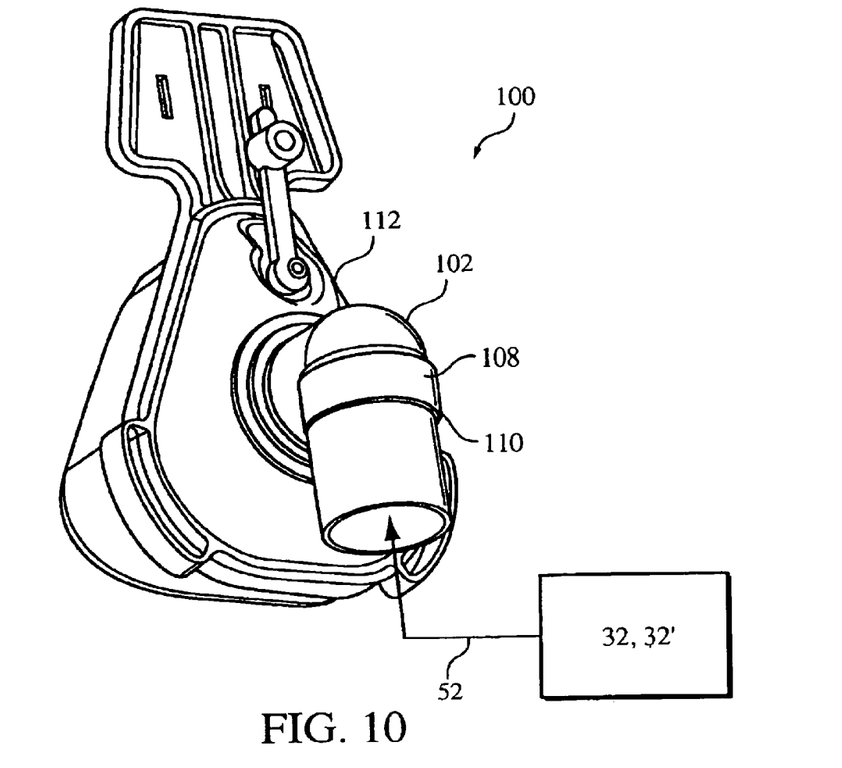
FIG. 10 is a perspective view of a mask and exhaust port assembly according to a second embodiment of the present invention.
Figure 11:
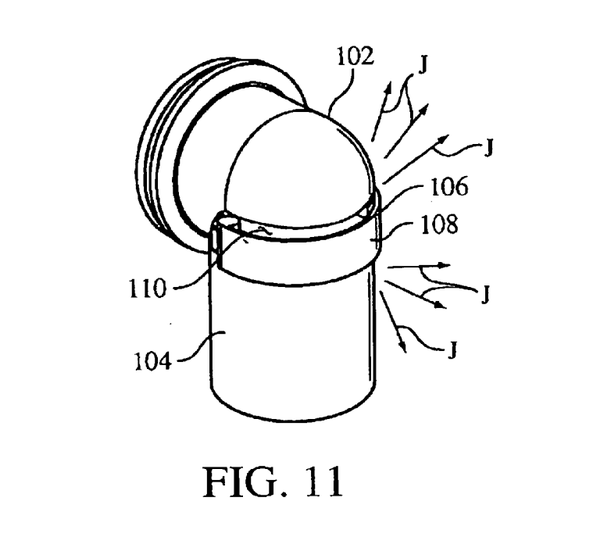
FIG. 11 is a perspective view of the exhaust port assembly of FIG. 10.

FIG. 10 schematically illustrates a second embodiment of a pressure support system 100 according to the principles of the present invention. Pressure support system 100 includes a pressure generating system 32, 32', a patient interface device 46, a patient circuit 52, and second embodiment of an exhaust port assembly 102. As noted above, pressure generating system 32, 32' corresponds to any conventional pressure generating system, such as those discussed above with respect to FIGS. 1 and 2. Similarly, the present invention contemplates that patient interface device 46 corresponds to any conventional patient interface device. For illustration purposes the patient interface device shown in FIG. 10 is a nasal mask that covers only the user's nose.

Exhaust port assembly 102, as shown in greater detail in FIGS. 11–15, includes a conduit 104 having a slot 106 defined therein, and a cap 108 that covers slot 106 such that a gap 110 is defined between the edge of the cap and the edge of the slot. Cap 108 is sized to as to have the same width as slot 106, so that cap 108 does not overlap over conduit 104 and yet fully covers slot 106. Moreover, cap 108 is configured and attached to conduit 104 such that the cap does not lie in the same plane as the conduit, but is maintained in a position so that it is spaced apart from the conduit.

By having the cap fully cover the slot and by raising the cap above the conduit, gap 110 defined therebetween is not merely a slot in the conduit, as is known in conventional exhalation ports, where the hole or slot in the conduit tends to direct or concentrate the flow of gas from the conduit. Similarly, because the cap does not overlap the conduit, there again is not directing or concentrating of the flow back along the conduit, as in the case with the devices taught by U.S. Pat. Nos. 5,937,851 and 6,112,745 to Lang, and published PCT application no. WO 00/78381.

Instead, this configuration of the present invention provides a relatively direct path from the interior of conduit 104 to the ambient atmosphere between the edges of the cap and the edge of the conduit defining the slot. As perhaps best shown in FIGS. 14 and 15, the edge of the cap and the edge of the conduit defining slop 106 are in an abutting configuration, so that a flow of exhaust gas is pinched as it passes through gap 110, as indicated by arrow I. Consequently, the flow of exhaust gas is dispersed over a relatively large area, as indicated by arrows J, into the ambient atmosphere. This relatively broad dispersion of gas from gap 10 allows for an extremely quiet flow of exhaust gas and the present invention accomplishes this function using only a relatively small area proximate to an end 112 of conduit 104 to which a patient interface is attached, thereby minimizing deadspace in the patient circuit.

Figure 12:
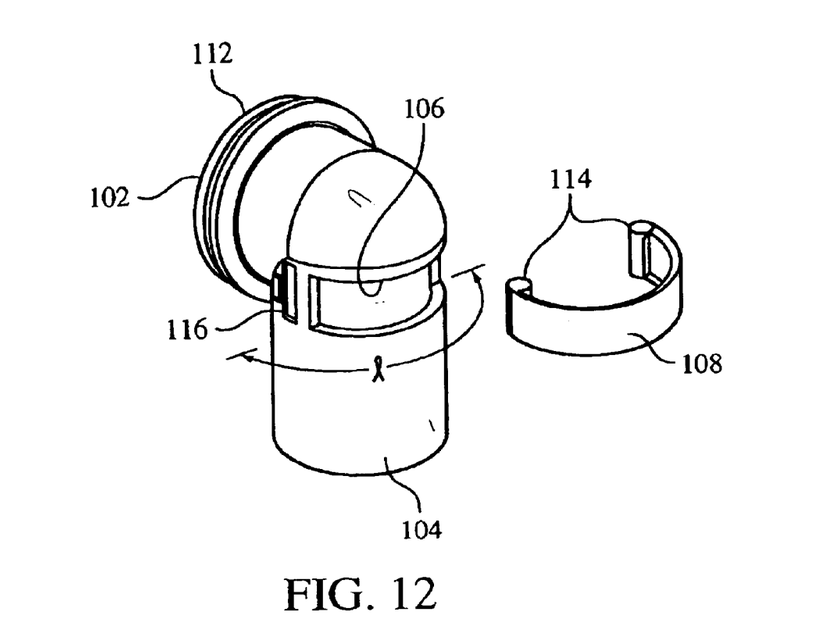
FIG. 12 is an exploded view of the exhaust port assembly of FIG. 10.
Figure 13:
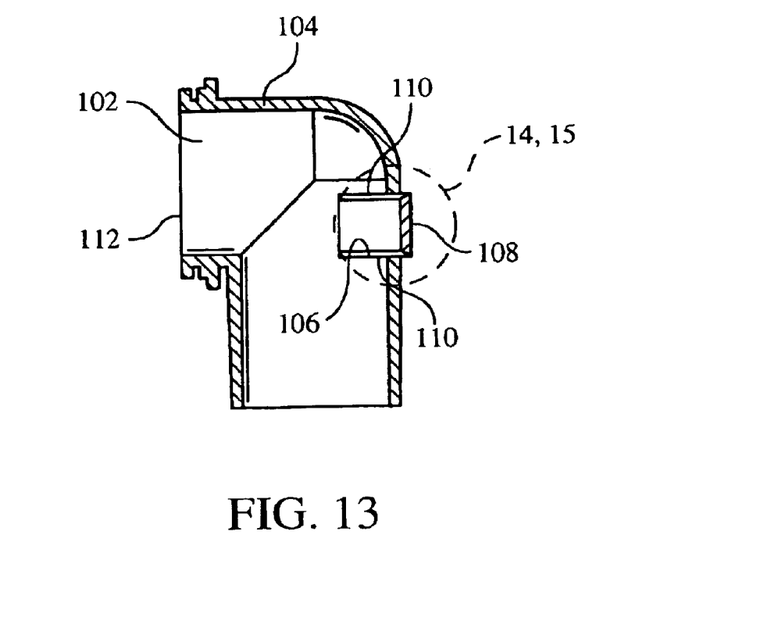
FIG. 13 is a cross-sectional view of the exhaust port assembly of FIG. 10.
Figure 14:
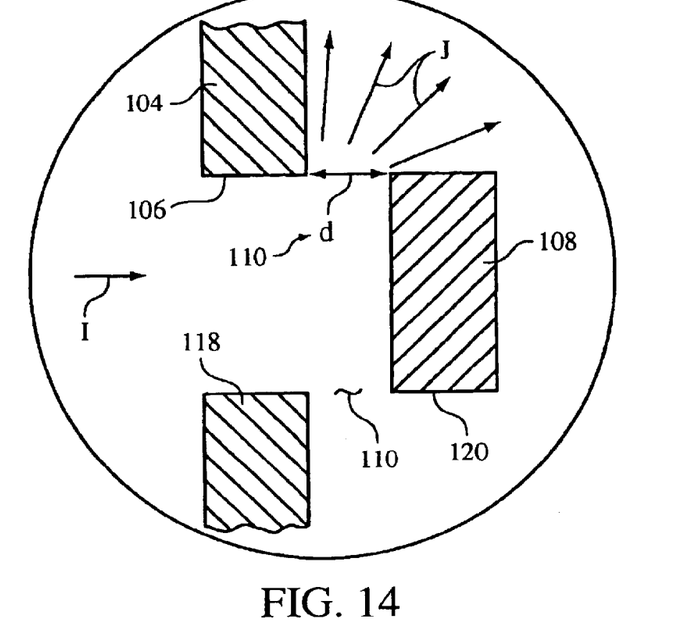
FIG. 14 is a detailed cross-sectional view of a first embodiment of a portion of the exhaust port assembly of FIG. 13.
Figure 15:
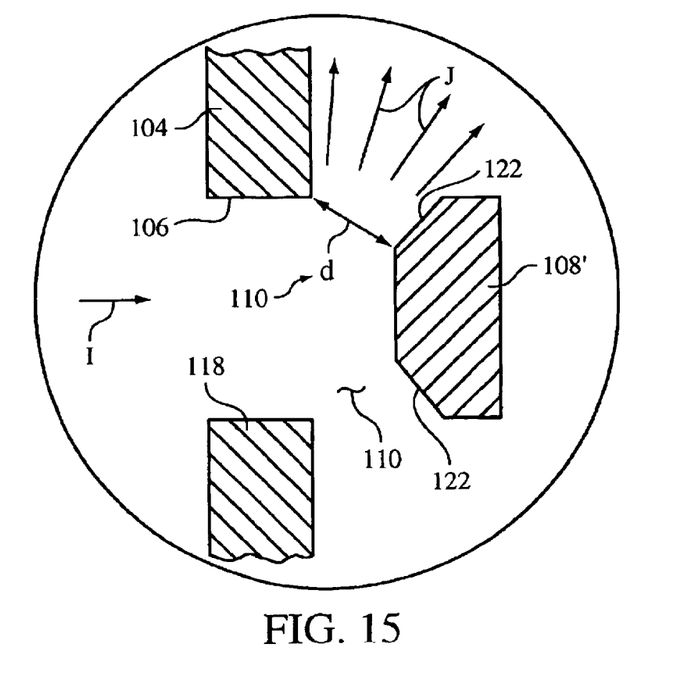
FIG. 15 is a detailed cross-sectional view of a second embodiment of a portion of the exhaust port assembly of FIG. 13.

The total exhaust area, which corresponds to the total size of gap 110, is a function of the size d of the gap, see FIGS. 14 and 15, and the length 1 of slot 106, see FIG. 12. As with exhaust port 60 of FIGS. 3–9, the total exhaust area of exhaust port assembly 100 preferably corresponds to that found in conventional exhaust port assemblies. Of course, the total exhaust area can vary depending on the desired rate of exhaust flow.

In a preferred embodiment of the present invention, the size d of gap 110 is not greater than 0.020 in. It has been determined that if gap size d exceeds this length, the gas dispersing properties of this embodiment for the exhaust port are not maximized. The lower limit for the size of gap d, however, is only limited by manufacturing tolerances. Over this range of sizes for gap d, the length of the gap can be selected so achieve a desired exhaust flow for a certain pressure within the conduit. For example, in one conventional pressure support system, the effective exhaust flow is selected to be between 67 lpm and 7.5 lpm, when the pressure within the conduit is 40 and 1.5 cmH$_2$O, respectively. In a preferred embodiment of the present invention, this exhaust flow over this range of pressures is achieved by providing two gaps, each having a distance of 0.0075 in. and each having a length of 1.266 in. It can be appreciated, that if higher exhaust flow rates are desired at these operating pressure, this can be accomplished by increasing the length of the gap, e.g., by increasing the number of gap, while keeping the gap distance d no more than 0.020 in.

It can be appreciated, for example, that the size d of gap 110 can be decreased or increased. However, if the rate of exhaust, i.e., the exhaust flow, is to remain unchanged, the length 1 of the gap should be correspondingly increased or decreased to provide substantially the same exhaust path area. It is preferable, however, that the size d of gap 110 not exceed 0.020 in., because beyond this size, the gas diffusing attribute of this exhaust path structure is no longer maximized.

In the illustrated exemplary embodiment of the present invention, cap 108 selectively attaches to conduit 104 over slot 106 so that there are two gaps 110, one on each side of the cap. The present invention, however, contemplates attaching the cap or configuring the cap or conduit, so that only one gap is formed as the exhaust path, thereby effectively reducing the length 1 of the gap. Of course, this will reduce the exhaust flow unless the length 1 of the gap and/or the size d of the gap is increased. Similarly, the present invention contemplates providing multiple slots and caps to provide more than two gaps for the exhaust flow.

The number of slot and caps can be used to determine the overall exhaust area desired. Thus, this embodiment of the present invention provides the user with great degree of flexibility in adjusting the exhaust rate by providing a plurality of slots in the conduit, and either completely blocking one or more of the slots with a cap and leaving at least one other slot unblocked to define a gap 110 having the desired exhaust area. For example, the present invention contemplates providing three caps fixed over three slots defined in the conduit. If the user wants the maximum exhaust flow, cap 108 can be provided over each slot so that there are six gaps 110. The exhaust flow can then be reduced by replacing a cap with a larger cap that completely or partially blocks the underlying slot.

In the illustrated embodiment, cap 108 is attached to conduit 104 via a tongue-and-groove configuration. For example, FIG. 12 illustrates a tongues 114 provided at each end of cap 108 and grooves 116 provided at corresponding locations on conduit 104. Of course, this configuration can be reversed, with the tongue provided on conduit 104 and the groove provided on cap 108. The present invention contemplates other techniques for securing cap 108 to conduit 104. For example, cap 108 can take the form of sleeve that slides over conduit 104 for positioning over slot 106. Regardless of the manner in which the slot is covered to define a gap 110, the size of the gap should be fixed and not change despite variations of the pressure within the conduit. That is, cap 108 should be attached to conduit 104 so that distance d between the edge of the cap and the edge of the conduit remain a fixed distance apart despite pressure variations within conduit 104.

While the figures illustrate the cap and slot as being configured such that gap 110 has a strait, arcuate shape, it is to be understood that other configurations for gap 110 are contemplated by the present invention. For example, the slot and cap can be configured so that the gap formed therebetween is elliptical, wavy, zigzag or any other shape, so long as the size of the gap is selected so as to maintain the advantageous gas diffusing properties noted above.

FIG. 14. illustrates, in detail, an edge 118 of slot 106 and an edge 120 of cap 108. In this embodiment, edges 118 and 120 are both generally strait. However, as shown in FIG. 15, the present invention contemplates providing a chamfered or beveled edge 122 as an edge for cap 108'. It is believed that chamfered edge 122 further enhances the gas diffusing properties and, hence, noise reduction of the exhaust port. The present invention further contemplates that edges 118 of slot 106 can be chambered or both edges 118 and 120 can be chamfered.

Figure 16:
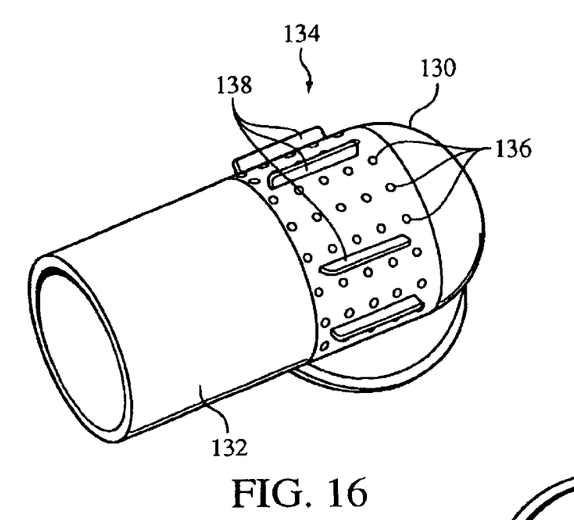
FIGS. 16 and 17 are perspective view and FIG. 18 is a side view of a third embodiment of an exhaust port assembly 130 according to the principles of the present invention.
Figure 17:
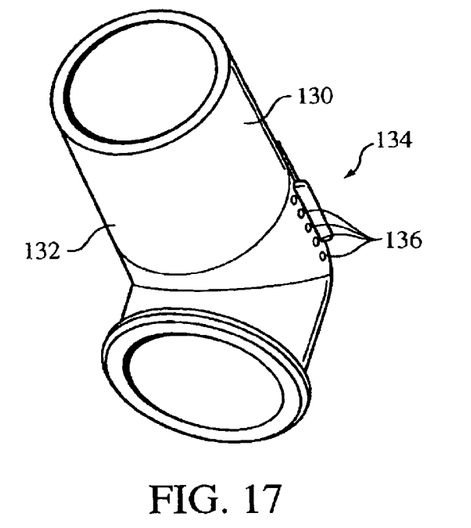
Figure 18:
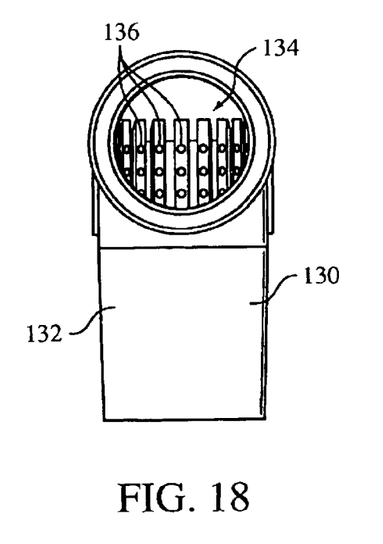

FIGS. 16, 17, and 18 illustrate a third embodiment of an exhaust port assembly 130 according to the principles of the present invention. Exhaust port assembly 130 includes a conduit 132 and a venting structure 134, also referred to as a venting means, for venting a flow of exhaust gas from within the conduit to ambient atmosphere a plurality of holes. As with the embodiment shown in FIGS. 3–9, the venting structure in exhaust port assembly 130 is defined by a plurality of fixed diameter holes 136. These holes are formed through conduit 132 so that a continuous flow of exhaust gas escapes from within the exhaust port assembly to ambient atmosphere. Protrusions 138 are provided among the pattern of holes to prevent the holes from becoming blocked.

The number, size, shape, and spacing of holes 136 are selected as discussed above with respect to the embodiment shown in FIGS. 3–9. However, holes 136 are not formed in a planar surface as in the embodiment shown in FIGS. 3–9. Instead, holes 136 are defined around a periphery of conduit 132.

In the illustrated embodiment, holes 136 are formed in the side of conduit 132 that is opposite the side to which the patient interface device attaches. In addition, holes 136 are configured in a pattern around the conduit over a range of approximately 180°. It is to be understood, however, that other ranges of angles for the pattern of holes about the periphery of the conduit are contemplated by the present invention as well as other patterns. However, it is preferable that the holes are arranged so as to diffuse the gas exhausted from the conduit as much as possible while directing the gas away from the patient.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. An exhaust port assembly comprising:

a conduit having a first end and a second end and adapted to carry a flow of gas, wherein the conduit is generally cylindrical shaped; and venting means, disposed between the first end and the second end of the conduit and having a fixed area, for venting a flow of exhaust gas from within the conduit to ambient atmosphere while 1) minimizing noise associated with the flow of exhaust gas passing to atmosphere, 2) diffusing the flow of exhaust gas passing to ambient atmosphere over a relatively large area, and 3) minimizing the area occupied by the venting means on the conduit, wherein the venting means comprises an opening defined in the conduit and a cap disposed in a fixed position over the conduit such that the cap does not move relative to the conduit during changes in pressure within the conduit, and having substantially the same width as the opening, wherein the cap overlies the opening so that a gap is defined between an edge of the cap and an edge of the opening, and wherein the gap extends a first length along at least a portion of the conduit, and wherein the opening is an arcuate slot having a length that extends around at least a portion of a perimeter of the conduit.

2. The exhaust port assembly of claim 1, further comprising a cap attaching assembly adapted to selectively attach the cap to the conduit.

3. The exhaust port assembly of claim 1, wherein the cap and the conduit are sized and configured such that the gap is not larger than 0.020 in.

4. The exhaust port assembly of claim 1, wherein an edge of the cap, an edge of the conduit, or both defining the gap are chamfered.

5. A pressure support system comprising:
    a) a pressure generating system adapted to generate a flow of breathing gas;
    b) a patient circuit having a first end coupled to the pressure generating system and a second end, wherein the conduit is adapted to carry the flow of gas;
    c) a patient interface device adapted to communicate the flow of breathing gas to an airway of a patient; and
    d) an exhaust port assembly associated with the patient circuit, the exhalation port assembly comprising:
        1) a conduit having a first end coupled to the patient interface device and a second end and adapted to be coupled to the patient circuit so that the conduit is disposed in-line in the patient circuit, wherein the conduit is generally cylindrical shaped; and
        2) venting means, disposed between the first end and the second end of the conduit and having a fixed exhaust area, for venting a flow of exhaust gas from within the conduit to ambient atmosphere while (i) minimizing noise associated with the flow of exhaust gas passing to atmosphere, (ii) diffusing the flow of exhaust gas passing to ambient atmosphere over a relatively large area, and (iii) minimizing the area occupied by the venting means on the conduit, wherein the venting means comprises an opening defined in the conduit and a cap disposed in a fixed position over the opening such that the cap does not move relative to the conduit during changes in pressure within the conduit, and having substantially the same width as the opening, wherein the cap overlies the opening so that a gap is defined between an edge of the cap and an edge of the opening, wherein the gap extends a first length along at least a portion of the conduit, and wherein the opening is an arcuate slot having a length that extends around at least a portion of a perimeter of the conduit.

6. The system of claim 5, wherein the cap and the conduit are sized and configured such that the gap is not larger than 0.020 in.

7. The system of claim 5, wherein an edge of the cap, an edge of the conduit, or both defining the gap are chamfered.

8. An exhaust port assembly comprising:

a conduit having a first end and a second end and including an opening defined in the conduit between the first end and the second end, wherein the conduit is generally cylindrical shaped; and a cap disposed in a fixed position over the opening such that the cap does not move relative to the conduit during changes in pressure within the conduit, and having substantially the same width as the opening, wherein the cap overlies the opening so that a gap is defined between an edge of the cap and an edge of the opening, wherein the gap extends a first length along at least a portion of the conduit, and wherein the opening is an arcuate slot having a length that extends around at least a portion of a perimeter of the conduit.

9. The exhaust port assembly of claim 8, further comprising a cap attaching assembly adapted to selectively attach the cap to the conduit.

10. The exhaust port assembly of claim 8, wherein the cap and the conduit are sized and configured such that the gap is not larger than 0.020 in.

11. The exhaust port assembly of claim 8, wherein an edge of the cap, an edge of the conduit, or an edge of both the cap and the conduit defining the gap are chamfered.

* * * * *